US00PP26305P3

(12) United States Plant Patent
Dirr et al.

(10) Patent No.: US PP26,305 P3
(45) Date of Patent: Jan. 12, 2016

(54) ***BUDDLEIA* PLANT NAME 'PIIBD-I'**

(50) Latin Name: ***Buddleia davidii* Franch.**
Varietal Denomination: PIIBD-I

(71) Applicants: Michael A. Dirr, Bogart, GA (US); Joshua H. Kardos, Watkinsville, GA (US)

(72) Inventors: Michael A. Dirr, Bogart, GA (US); Joshua H. Kardos, Watkinsville, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 101 days.

(21) Appl. No.: 13/998,258

(22) Filed: Oct. 16, 2013

(65) Prior Publication Data

US 2015/0106987 P1 Apr. 16, 2015

(51) Int. Cl.
*A01H 5/02* (2006.01)

(52) U.S. Cl.
USPC ..... Plt./242
CPC ..... *A01H 5/02* (2013.01)

(58) Field of Classification Search
USPC ..... Plt./242
See application file for complete search history.

*Primary Examiner* — Keith O. Robinson
(74) *Attorney, Agent, or Firm* — Lathrop & Gage LLP

(57) ABSTRACT

A new and distinct cultivar of *Buddleia* plant named 'PIIBD-I', characterized by its compact, rounded to upright growth habit, dark green foliage, dark violet-purple flowers with an orange center, and long flowering season, with flowers produced from summer to the first frost.

2 Drawing Sheets

Genus and species of plant claimed: *Buddleia davidii* Franch.

Variety denomination: 'PIIBD-I'.

BACKGROUND OF THE INVENTION

The present invention relates to a new and distinct cultivar of *Buddleia* plant, botanically known as *Buddleia davidii* Franch., commonly known as butterfly-bush, and hereinafter referred to by the cultivar name 'PIIBD-I'. 'PIIBD-I' is grown primarily as an ornamental for landscape use and for use as a potted plant.

'PIIBD-I' originated from an open-pollination of the cultivar 'Griffin Blue' (unpatented) growing in Watkinsville, Ga. in 2010. The cultivar 'PIIBD-I' originated and was selected in a cultivated environment in Watkinsville, Ga. from the progeny of this open-pollination by continued evaluation for growth habit, foliage and flower characteristics.

Asexual reproduction of 'PIIBD-I' by stem cuttings in Watkinsville, Ga. since 2011 has shown that all the unique features of this new *Buddleia,* as herein described, are stable and reproduced true-to-type through successive generations of such asexual propagation.

SUMMARY OF THE INVENTION

Plants of the new cultivar 'PIIBD-I' have not been observed under all possible environmental conditions. The phenotype may vary somewhat with changes in light, temperature, soil and rainfall without, however, any variance in genotype.

The following traits have been observed and represent the characteristics of the new cultivar. In combination these characteristics distinguish 'PIIBD-I' from all other varieties in commerce known, to the inventor. 1. Compact, rounded to upright growth habit; 2. Dark green foliage; 3. Dark violet-purple flowers with an orange center; 4. Long flowering season, with flowers produced from summer to the first frost.

'PIIBD-I' is distinguished from its female parent, 'Griffin Blue', by its overall size, foliage color, flower color and inflorescence size. 'PIIBD-I' has an overall smaller size, dark green foliage, violet-purple flower color and larger inflorescences, whereas 'Griffin Blue' has an overall larger size, gray-green foliage, violet-blue flower color and smaller inflorescences.

'PIIBD-I' can be compared to 'Guinevere' (unpatented), but differs in the following characteristics. 'PIIBD-I' has dark green foliage, darker violet-purple flowers and smaller inflorescences, whereas 'Guinevere' has dark blue-green foliage, lighter violet-purple flowers and larger inflorescences.

BRIEF DESCRIPTION OF THE DRAWINGS

The accompanying color photographs illustrate the flower and foliage characteristics and the overall appearance of 'PIIBD-I', showing the colors as true as it is reasonably possible to obtain in color reproductions of this type. Colors in the photographs may differ slightly from the color values cited in the detailed botanical description which accurately describe the colors of the new *Buddleia.*

DETAILED DESCRIPTION

Figure 1:
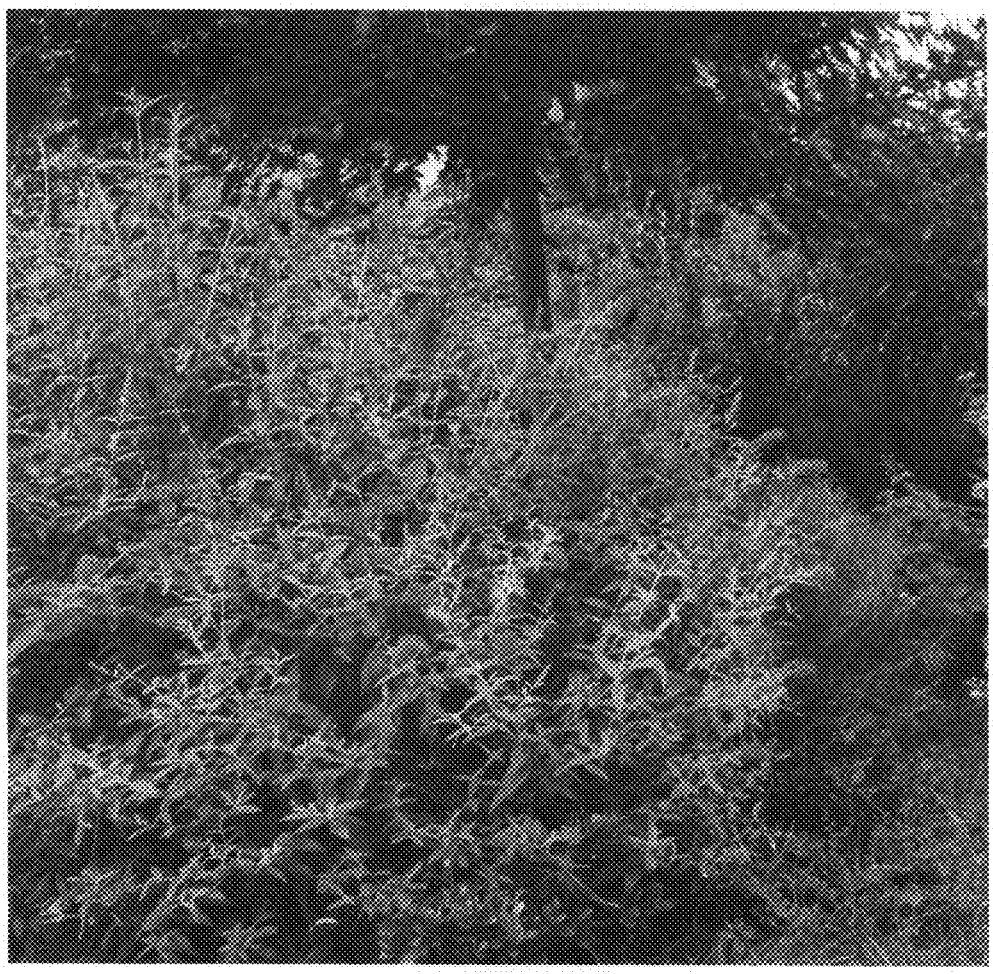
FIG. 1 Illustrates the overall appearance of a plant that is three years old of 'PIIBD-I' planted in the ground.
Figure 2:
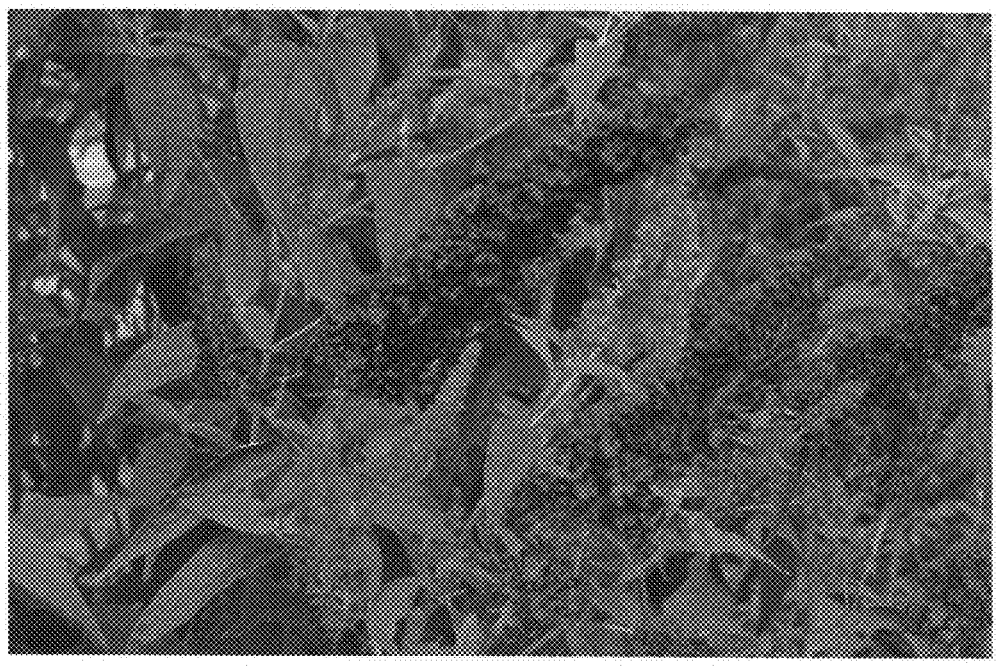
FIG. 2 Illustrates a close-up view of the inflorescences on a three year old plant of 'PIIBD-I'.

In the following description, color references are made to The Royal Horticultural Society Colour Chart, 2007 Edition, except where general terms of ordinary dictionary significance are used. The plant used for the description was approximately three years old and was grown in the ground in a nursery in Watkinsville, Ga. Colors are described using The Royal Horticultural Society Colour Chart (R.H.S.).

Botanical classification: *Buddleia davidii* Franch. 'PIIBD-I'.

Parentage:

*Female, or seed, parent.*—'Griffin Blue' (unpatented).

*Male, or pollen parent.*—Unknown (open-pollinated).

Propagation: terminal cuttings.

Time to initiate roots, summer: about 21 days at 32° C.

Time to produce a finished plant, summer: about 12 weeks from softwood cuttings.

Plant description: Deciduous flowering shrub; compact, rounded to upright growth habit. Freely branching; pruning enhances lateral branch development.

*Root description.*—Numerous, fibrous and well-branched. Color: 161C.

*Plant size.*—About 203 cm high from the soil level to the top of the inflorescences and about 254 cm wide. First year stems have a diameter of about 4 mm. Shape: quadrangular when young, becoming rounded with age. Pubescence: tomentulose when young, becoming glabrous with age. Second year and older stems have a diameter of about 5 mm or more. Shape: round.

*Trunk diameter.*—3.3 cm at the soil line. Color: 199A.

*Internode length.*—About 4.3 cm.

*Strength.*—Flexible when young, becoming stronger with age.

*First year stem color* (*young*).—148C. Color (mature): 199B.

*Second year and older stem color.*—199A. Bark does not exfoliate.

*Lateral branches*.—Approximately 80. Length about 60 to 70 cm. Internode length 4.3 cm. Diameter about 4.5 mm. Color on younger branches 148C. Color on older branches 199A. Strength strong and somewhat flexible. Younger branches are pubescent, becoming glabrous with age.

Vegetative buds: Opposite arrangement, naked, subglobose, 2 bud scales with tomentulose pubescence.

*Color.*—195B.

*Size.*—About 2 mm in length and 1 mm in width.

Foliage description:

*Quantity of leaves per branch*.—About 14-22.

*Arrangement.*—Opposite, simple.

*Leaf length.*—About 8.8 cm.

*Leaf width.*—About 2.9 cm.

*Shape.*—Ovate-lanceolate to lanceolate.

*Apex.*—Acuminate.

*Base.*—Cuneate.

*Margin.*—Closely serrate to serrulate.

*Texture.*—Upper surface is glabrous, lower surface is tomentose.

*Venation pattern.*—Pinnate.

*Venation color* (*upper surface*).—143B.

*Venation color* (*lower surface*).—144B.

*Foliage color* (*upper surface*).—N137A.

*Foliage color* (*lower surface*).—191C.

*Petiole length.*—About 4 mm.

*Petiole diameter.*—About 1 mm.

*Petiole color.*—144B.

*Pubescence.*—Tomentulose.

*Leaf blade*.—Variegation absent.

Flower description: Flowers on new growth. Flowers are produced from about June through the first frost in Watkinsville, Ga. An inflorescence is showy for about three weeks, and individual flowers are salverform in shape and last about three days and are self-cleaning. Approximately 285 flowers per individual inflorescence.

*Inflorescence type.*—Terminal panicle.

*Inflorescence shape.*—Globose.

*Inflorescence length.*—About 11.3 cm.

*Inflorescence width.*—About 3.7 cm.

*Fragrance.*—Pleasant and sweet.

*Peduncle.*—About 9.8 cm in length, about 2 mm in diameter, strength-strong, color is N186C, with tomentulose pubescence.

*Individual flowers.*—About 1.3 cm in height and 8 mm in diameter and salverform in shape.

*Flower buds.*—Length: about 8 mm; Diameter: about 2 mm; Color: 79A. Shape: elongated, linear balloon.

*Pedicels.*—About 2.5 mm in length, less than 1 mm in diameter, strength-moderately strong, 195A in color with tomentulose pubescence.

*Calyx.*—Consists of 4 sepals fused at the base. The calyx is about 3 mm in length, about 1 mm in diameter, 148C in color, tubular in shape with tomentulose pubescence. The individual sepals are lanceolate in shape, with an acute apex and entire margin, 148C in color with tomentulose pubescence.

Petals:

*Arrangement/appearance.*—4 petals fused at the base to form the corolla tube, which is about 1 cm in length, 1.5 mm in width, outer surface is 72B in color and the inner surface or center of the flower is 25B in color.

*Petal.*—Length: about 4 mm. Width: about 4 mm. Shape: broad spatulate. Apex: broad obtuse to rounded. Margin: ruffled. Texture: glaucous.

*Petal color.*—Upper surface is N81A in color and lower surface is 77A in color.

*Corolla*.—Throat is about 9 mm in length, less than 1 mm in width, corolla tube color inside is 25B, corolla tube color outside is 63B, corolla tube surfaces pubescent, corolla tube shape is tubular, corolla lobe is semi-erect at full flowering and arrangement is free, present is an eye and it is 25B in color.

Stamens:

*Quantity/arrangement.*—4 stamens per flower, fused to the inner base of the corolla tube, about 4 mm long.

*Filaments.*—3 mm in length, less than 0.5 mm in width, and 1B in color.

*Anthers.*—1 mm in length, 0.5 mm in width, and 4C in color. The stamens are not pubescent.

*Pollen.*—Produced in small quantities and is 158D in color.

Pistils:

*Quantity.*—One superior pistil per flower.

*Pubescence.*—None.

*Pistil.*—About 5 mm in length and about 1 mm in width.

*Stigma.*—Elongated shape, about 1.5 mm in length and 0.5 mm in width and 144B in color.

*Style.*—Tubular in shape, about 1 mm in length, less than 0.5 mm in width and 77D in color.

*Ovary.*—Ovoid in shape, about 2.5 mm in length, about 1 mm in width and 144B in color.

Fruit:

*Type/appearance.*—Two-valved, septicidally dehiscent capsule.

*Length.*—About 7 mm.

*Width.*—About 2 mm.

*Immature color.*—144C.

*Mature color.*—N200D. Each capsule contains many tiny seeds 165D in color.

Disease/pest resistance: 'PIIBD-I' has not exhibited any particular pest or disease susceptibility or resistance, except occasional susceptibility to spider mites (*Tetranychus urticae*) under very hot and dry conditions. 'PIIBD-I' is cold hardy to USDA Hardiness Zones 5-9.

I claim:

1. A new and distinct *Buddleia* plant named 'PIIBD-I', as illustrated and described herein.

* * * * *